United States Patent [19]

Brune et al.

[11] Patent Number: 6,059,733
[45] Date of Patent: May 9, 2000

[54] METHOD OF DETERMINING A PHYSIOLOGICAL STATE OF A RUMINANT ANIMAL USING AN INGESTIBLE BOLUS

[75] Inventors: Scott A. Brune, Leo; Paul A. McAfee, Fort Wayne, both of Ind.

[73] Assignee: Innotek, Inc., Garrett, Ind.

[21] Appl. No.: 09/121,421

[22] Filed: Jul. 23, 1998

Related U.S. Application Data

[63] Continuation-in-part of application No. 08/918,607, Aug. 22, 1997.

[51] Int. Cl.$^7$ ........................................................ A61B 5/00
[52] U.S. Cl. ............................................ 600/549; 128/899
[58] Field of Search .............................. 600/549; 128/899

[56] References Cited

U.S. PATENT DOCUMENTS

| | | |
|---|---|---|
| D. 321,069 | 10/1991 | Stoddard, III . |
| 3,144,017 | 8/1964 | Muth . |
| 3,216,411 | 11/1965 | Watanuki et al. . |
| 3,229,684 | 1/1966 | Nagumo et al. . |
| 3,340,866 | 9/1967 | Noller . |
| 3,841,756 | 10/1974 | Groshowicz ............................ 356/72 |
| 3,893,111 | 7/1975 | Cotter . |
| 3,934,584 | 1/1976 | Corio ................................... 128/223 |
| 3,948,249 | 4/1976 | Ambrosini ........................... 128/2 H |
| 4,165,033 | 8/1979 | Nielsen et al. ....................... 235/439 |
| 4,206,766 | 6/1980 | Bielka ................................... 128/738 |
| 4,247,758 | 1/1981 | Rodrian ............................ 235/92 MS |
| 4,262,632 | 4/1981 | Hanton . |
| 4,305,402 | 12/1981 | Katims ................................. 128/741 |

(List continued on next page.)

FOREIGN PATENT DOCUMENTS

| | | |
|---|---|---|
| 649212 | 5/1994 | Australia . |
| 0 299 557 | 1/1989 | European Pat. Off. . |
| 0 395 188 | 10/1990 | European Pat. Off. . |
| 0 549 081 | 6/1993 | European Pat. Off. . |
| 83 09322 | 1/1984 | France . |
| 833599 | 5/1983 | South Africa . |
| 2 165 723 | 4/1986 | United Kingdom . |
| WO 8901722 | 2/1989 | WIPO . |
| PCT/US91/00104 | 7/1991 | WIPO . |
| WO 9517809 | 6/1995 | WIPO . |
| WO 98/01025 | 1/1998 | WIPO ........................... A01K 11/00 |

OTHER PUBLICATIONS

First page of U.S. Patent No. 3,557,758; Issued Jan. 26, 1971; Keith Malcolm Lack.
First page of U.S. Patent No. 4,232,682; Issued Nov. 11, 1980; George J. Veth.
"Summertime Heat and Its Effect Upon Dairy Herd Profitability"; T. H. White, Jr.; Apr. 1, 1986.
First page of U.S. Patent No. 4,992,794; Issued Feb. 12, 1991; Arnoldus M. Brouwers.
"Detecting Heat in Dairy Cows", R. E. Marcoot, et al.; Jun. 1992.
"Detecting Estrus in Dairy Cattle"; D. A. Colman; Oct., 1993.
"Injectable Electronic Identification"; Sidney L. Spahr; Oct., 1993.

*Primary Examiner*—Max Hindenburg
*Assistant Examiner*—Pamela L. Wingood
*Attorney, Agent, or Firm*—Taylor & Aust, P.C.

[57] ABSTRACT

A method of determining a physiological state of a ruminant animal monitors the core body temperature of the ruminant animal. A bolus including a temperature sensor and a transmitter is placed within a stomach of the ruminant animal. A plurality of temperatures are sensed within the stomach using the sensor, with each temperature representing a temperature at a respective discrete point in time over a time period. A plurality of air-borne signals are transmitted to a remote receiver using the transmitter, with each air-borne signal representing at least one of the sensed temperatures. The plurality of temperatures are mathematically analyzed at discrete points in time over the time period using the remote receiver. The physiological state of the ruminant animal is determined using the mathematically analyzed temperatures.

25 Claims, 4 Drawing Sheets

U.S. PATENT DOCUMENTS

| | | |
|---|---|---|
| 4,399,821 | 8/1983 | Bowers . |
| 4,411,274 | 10/1983 | Wright ................................. 128/738 |
| 4,471,354 | 9/1984 | Smith ............................... 340/870.17 |
| 4,493,290 | 1/1985 | Gibbard ............................... 119/51 R |
| 4,537,150 | 8/1985 | Bowers ............................... 119/14.17 |
| 4,750,490 | 6/1988 | Haw et al. ............................. 128/330 |
| 4,784,155 | 11/1988 | Mills ..................................... 128/734 |
| 4,844,076 | 7/1989 | Lesho et al. ........................... 600/549 |
| 4,854,328 | 8/1989 | Pollack ................................. 600/549 |
| 4,865,044 | 9/1989 | Wallace et al. ....................... 600/549 |
| 4,895,165 | 1/1990 | Blair ..................................... 128/738 |
| 5,024,221 | 6/1991 | Morgan . |
| 5,111,799 | 5/1992 | Senger et al. ......................... 128/738 |
| 5,217,011 | 6/1993 | Bish . |
| 5,241,924 | 9/1993 | Lundin et al. ...................... 119/51.02 |
| 5,415,181 | 5/1995 | Hogrefe et al. . |
| 5,481,262 | 1/1996 | Urbas ................................ 340/870.17 |
| 5,482,008 | 1/1996 | Stafford et al. . |
| 5,499,626 | 3/1996 | Wilham et al. . |
| 5,542,431 | 8/1996 | Starzl ..................................... 128/738 |
| 5,653,239 | 8/1997 | Pompei .................................. 128/664 |
| 5,697,384 | 12/1997 | Miyawaki .............................. 128/899 |

| COW ID | 5/11/98 | 5/12/98 | 5/13/98 | 5/14/98 | 5/15/98 | 5/16/98 | 5/17/98 | 5/18/98 |
|---|---|---|---|---|---|---|---|---|
| 518 | | | | | | | | |
| 525 | | | | | | | | |
| 535 | | | | | | | | |

Fig. 5

METHOD OF DETERMINING A PHYSIOLOGICAL STATE OF A RUMINANT ANIMAL USING AN INGESTIBLE BOLUS

CROSS REFERENCE TO RELATED APPLICATIONS

This is a continuation-in-part of U.S. patent application Ser. No. 08/918,607, entitled INGESTIBLE ANIMAL TEMPERATURE SENSOR, filed Aug. 22, 1997.

BACKGROUND OF THE INVENTION

1. Field of the Invention

The present invention relates to a method of monitoring the core body temperature of an animal, and, more particularly, to a method of monitoring the core body temperature of a ruminant animal using an ingestible bolus.

2. Description of the Related Art

It is known to transmit a message in the form of an encoded data packet from a bolus placed within the stomach of a ruminant animal to a remote receiver unit in the form of a stationary base unit or a portable hand-held unit. For example, U.S. patent application Ser. No. 08/918,607 the parent application, describes a system for remotely monitoring a temperature sensed within the stomach of a cow. Such a system is a step forward in the art and allows a user to individually monitor the core body temperature of a plurality of cows in a herd.

Certain physiological states of a cow cause the core body temperature of the cow to vary somewhat relative to a normal core body temperature. For example, several hours before a cow is in standing heat and most likely to conceive, the core body temperature of the cow rises. The core body temperature of a cow may rise, e.g., approximately 0.5° F. about 12 hours before the cow is in standing heat. Additionally, the core body temperature of a cow may rise when the cow is sick, or when the cow is under heat stress associated with very hot ambient conditions. Conversely, the core body temperature of a cow drops shortly before the cow delivers a calf, when the cow is experiencing hypothermia, or when the cow is dead. The core body temperature of the cow is thus an indicator of several different physiological states.

One problem with utilizing an ingestible bolus to determine a core body temperature based upon a sensed temperature within the stomach of the cow is that the cow drinks quite a few times during the course of a day (e.g., 10 to 12 times a day) and ingests a relatively large quantity of water each day. The temperature of the water is, of course, typically much cooler than the core body temperature of the cow. Thus, each time the cow drinks the temperature sensed within the stomach plummets very fast dependent upon the amount and temperature of the water ingested. The temperature data which is received by the remote receiver unit thus varies over a relatively large range.

What is needed in the art is a method of analyzing temperature data associated with temperatures sensed within the stomach of a ruminant animal and a method of displaying the data or alerting the user of a physiological state or a physiological change of the ruminant animal.

SUMMARY OF THE INVENTION

The present invention provides a method of determining a physiological state of a ruminant animal by mathematically analyzing at least one portion of a history of data representing sensed temperatures within a stomach of the ruminant animal.

The invention comprises, in one form thereof, a method of determining a physiological state of a ruminant animal by monitoring the core body temperature of the ruminant animal. A bolus including a temperature sensor and a transmitter is placed within a stomach of the ruminant animal. A plurality of temperatures are sensed within the stomach using the sensor, with each temperature representing a temperature at a respective discrete point in time over a time period. A plurality of air-borne signals are transmitted to a remote receiver using the transmitter, with each air-borne signal representing at least one of the sensed temperatures. The plurality of temperatures are mathematically analyzed at discrete points in time over the time period using the remote receiver. The physiological state of the ruminant animal is determined using the mathematically analyzed temperatures.

An advantage of the present invention is that a physiological state of the ruminant animal can be remotely determined, thereby allowing the user to intervene or take proactive action based upon the determined physiological state.

Another advantage is that different physiological states of the ruminant animal can be determined.

Yet another advantage is that a simple user interface indicates present and past physiological states of the ruminant animal, without requiring data interpretation by the user.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 5 is a graphical illustration of an exemplary screen output of the remote receiver which visually indicates the physiological states of a number of ruminant animals.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
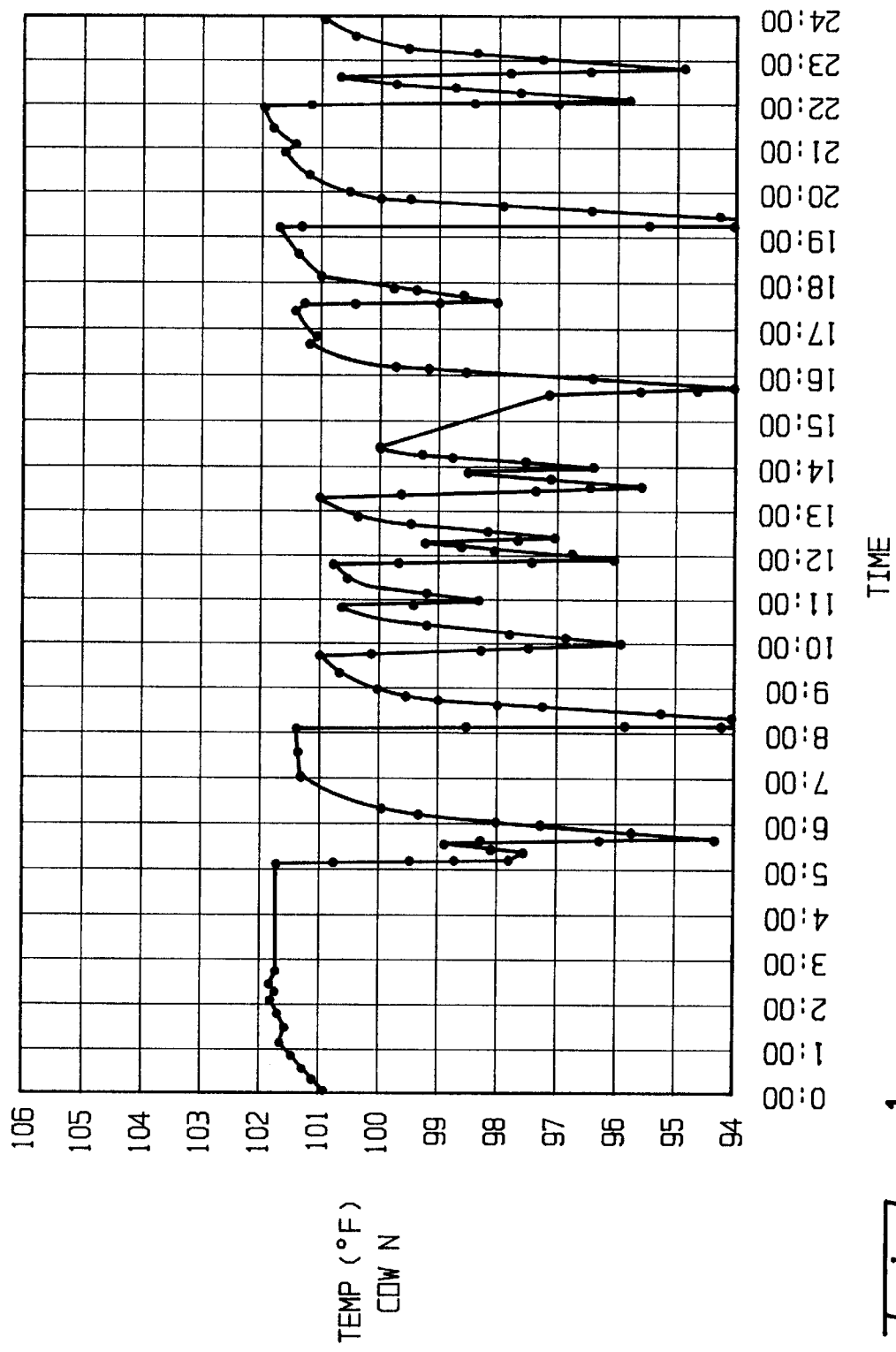
FIG. 1 is a graphical illustration of temperatures sensed within the stomach of a ruminant animal during a twenty-four hour period.

Referring now to the drawings and particularly to FIG. 1, there is shown a graphical illustration of a typical temperature profile within the stomach of a ruminant animal, such as a cow, during a 24-hour period. A normal core body temperature for a cow is between 101° and 102° F., usually about 101.5° F. As is apparent, the temperature within the stomach of the cow varies widely during the course of a day. This is primarily due to the ingestion of cool or cold water which the cow drinks during the day. Each time the cow drinks, the temperature within the stomach plummets. When the cow stops drinking the core body temperature of the cow immediately starts to raise the temperature within the stomach back to the core body temperature. If the cow drinks again before the temperature within the stomach reaches the core body temperature (such as occurred at approximately at 5:15 a.m. in the example shown), then the temperature within the stomach again plummets, dependent upon the temperature and quantity of the water ingested.

As is apparent from FIG. 1, the temperature profile within the stomach of a cow varies widely over any given 24-hour period. On the other hand, the change in the core body temperature of a cow associated with different physiological states, such as standing heat, sickness, heat stress and calving, does not vary over a large range, typically only ±0.25 to 2° F. The present invention of detecting a physiological state of the cow therefore mathematically analyzes and interprets the data associated with the temperature within the stomach of the cow to deduce a physiological state or physiological change of the cow.

In general, the present invention utilizes temperature data sensed by a bolus within the stomach of a cow to determine the physiological state of the cow. While one cow may drink more than another cow on an average, it has been found that each cow drinks a relatively steady amount of water during the course of a day from one day to another. Thus, the average temperature within the stomach of a cow remains relatively constant from one day to another, as long as the physiological state of the cow also remains constant. A change in the average temperature within the stomach of the cow also may indicate a change in the physiological state of the cow. In order to detect the physiological change, a history of average temperature data for a specific cow is determined. The data history for a specific cow is calculated over an extended period of time which is sufficient to provide an adequate profile of the cow. For example, the extended period of time may be several days, a week, a month, or even a season. This data history which is then used as a baseline is compared with stomach temperature data over a shorter period of time which allows an individual to properly react or intervene when a change in the physiological state of the cow is determined. For example, the shorter period of time may be a half day, one day, or a couple of days. The shorter period of time must be selected long enough to provide good data, but yet short enough to allow an individual to react or intervene in a timely manner.

Figure 2:
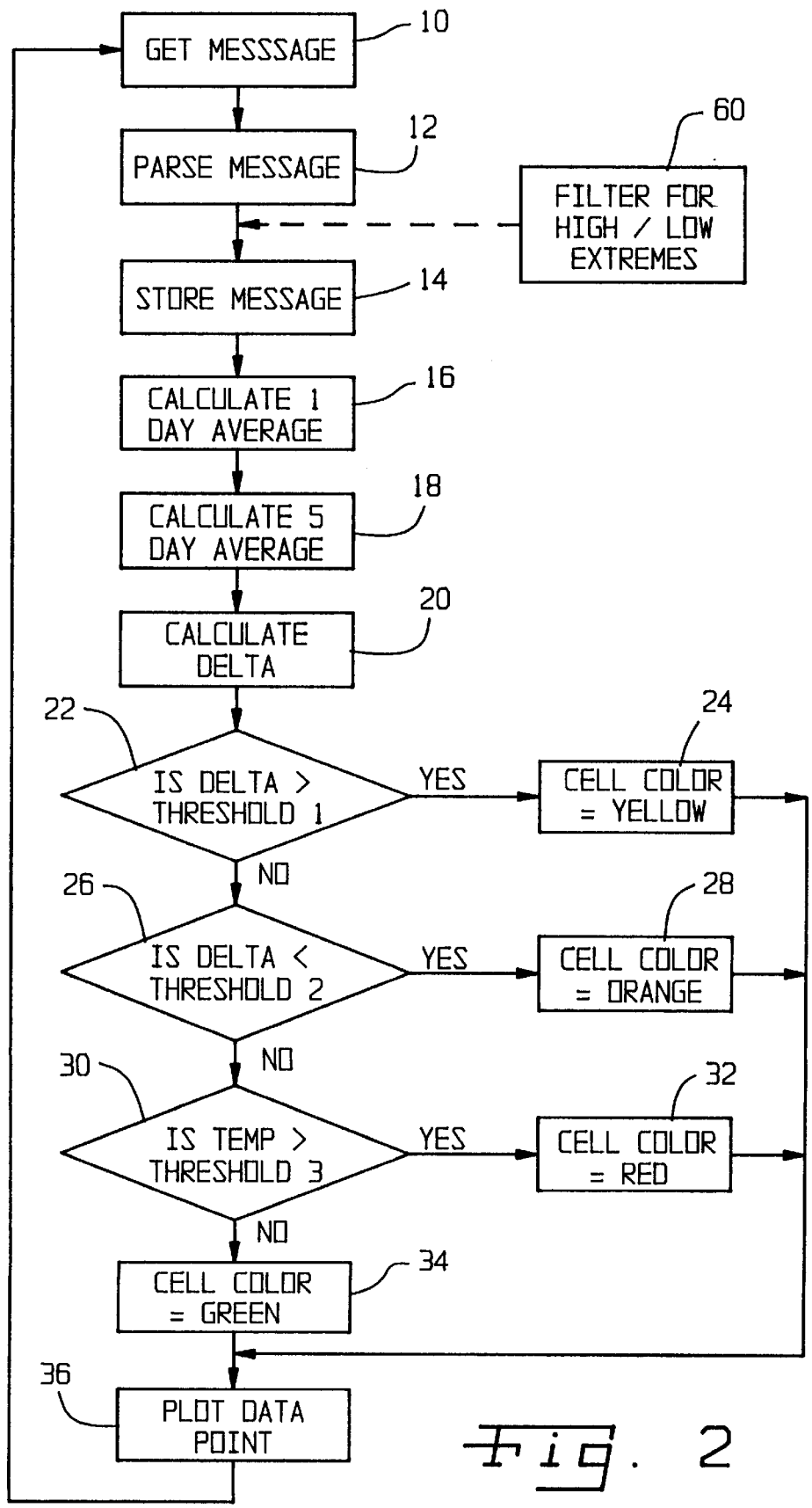
FIG. 2 is a flowchart illustrating an embodiment of the method of the present invention for determining a physiological state of the ruminant animal.

Referring now to FIG. 2, an embodiment of the method of the present invention for determining a physiological state of a cow will be described in greater detail. It is to be understood that the data is transmitted using an ingestible bolus (such as described in parent application Ser. No. 08/918,607 to a remote receiver which may be in the form of a stationary base unit or a portable hand-held unit. Unless otherwise noted, details familiar to persons skilled in the electronic arts will be omitted since they are extraneous detail and thus have no bearing on reducing the invention to practice. Moreover, it is also to be understood, and it will be appreciated by those skilled in the art, that the methodology and logic of the present invention described herein may be carried out using any number of structural configurations such as electronic hardware, software, and/or firmware or the like.

At block 10, the remote receiver receives a message in the form of an air-borne signal which is transmitted from a bolus implanted within the stomach of a cow. The message or signal is preferably in the form of a data packet represented by a number of data pulses. For each message, the data packet includes temperature data representing the sensed temperature within the stomach, identification data such as an identification number which is unique to the specific cow, and date and/or time stamp data corresponding to the discrete point in time at which the temperature was sensed by the bolus. In the embodiment shown, each data packet corresponds to a single sensed temperature within the stomach; however, it is also possible for a data packet to include data corresponding to multiple sensed temperatures and associated discrete times of sensing. At block 12, the message or data packet received by the remote receiver is parsed to segregate and ascertain the temperature data, identification data and time stamp data. The parsed data is then stored in a memory device, such as a RAM memory and/or non-volatile long-term storage memory (block 14). In the embodiment shown, the parsed message is stored both in a RAM memory and a long-term storage memory such as a hard drive.

Figure 3:
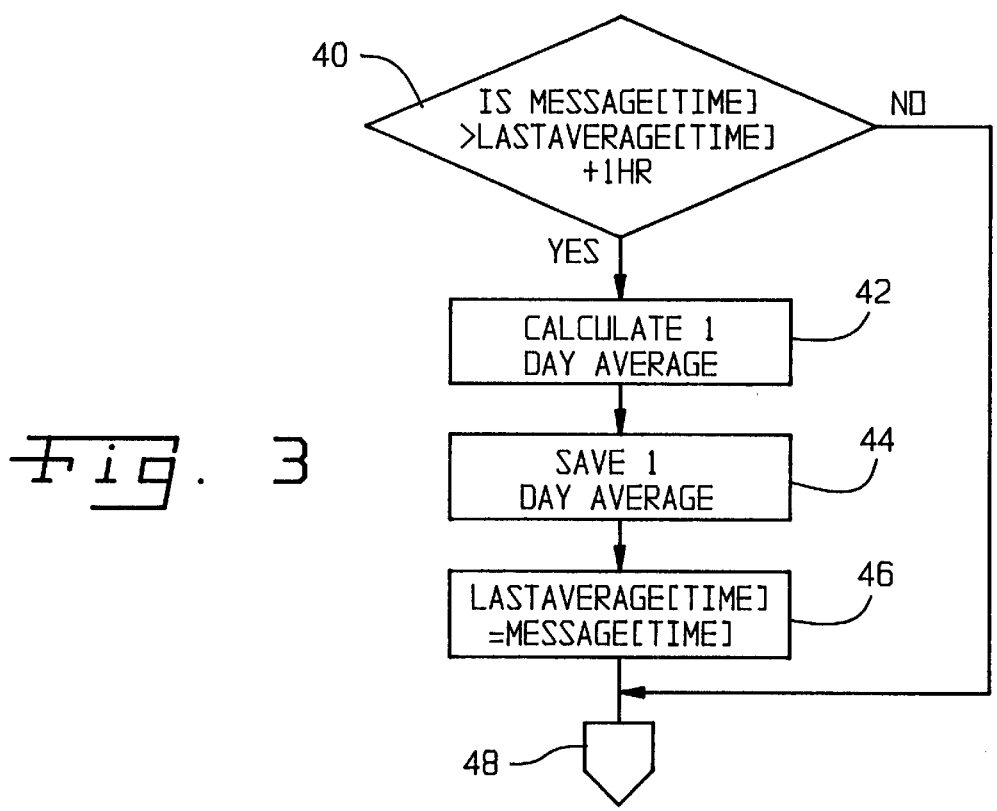
FIG. 3 is a flowchart illustrating an embodiment of the method of the present invention for determining a one day average of the core body temperature of the ruminant animal.

At block 16, a one day average of the temperatures sensed over a one-day (i.e., 24 hour) time period is calculated. Reference is hereby made to FIG. 3 for a more detailed explanation of the calculation of a one day average. In general a one day average temperature is only calculated using the procedure in blocks 40–46 if the time stamp on the parsed message is at least one hour past a previous calculation of the one day average. More particularly, the variables MESSAGE[TIME] and LASTAVERAGE[TIME] each correspond to pointer values in a memory, such as a RAM memory. The point value MESSAGE[TIME] points to a location in memory in which the time stamp data for the current message is located, and the pointer value LASTAVERAGE[TIME] points to a location in memory in which the time stamp data is located for the last one day average temperature calculation. If the time stamp data at the pointer value MESSAGE[TIME] is not greater than the time stamp data plus one hour located at the pointer value LASTAVERAGE[TIME], then a one day average is not calculated and the procedure ends at 48. On the other hand, if the value of the time stamp data in the memory location MESSAGE[TIME] is more than one hour greater than the value of the time stamp data in the memory location LASTAVERAGE[TIME], then a one day average temperature is calculated in block 42. The one day average is calculated by adding up all the sensed temperature values for the last 24 hours. That is, the 24-hour period is a sliding window calculated backwards from the time stamp data contained in MESSAGE[TIME]. The total value of all the temperatures for the last 24 hours is then divided by the total number of temperatures for the last 24 hours (i.e., the number of parsed messages received in the last 24 hours for that particular cow). The one day average temperature is then saved to memory (block 44), preferably both hard drive and RAM memory. The pointer value LASTAVERAGE [TIME] is then changed to point to the memory location containing the time stamp data at MESSAGE[TIME].

Figure 4:
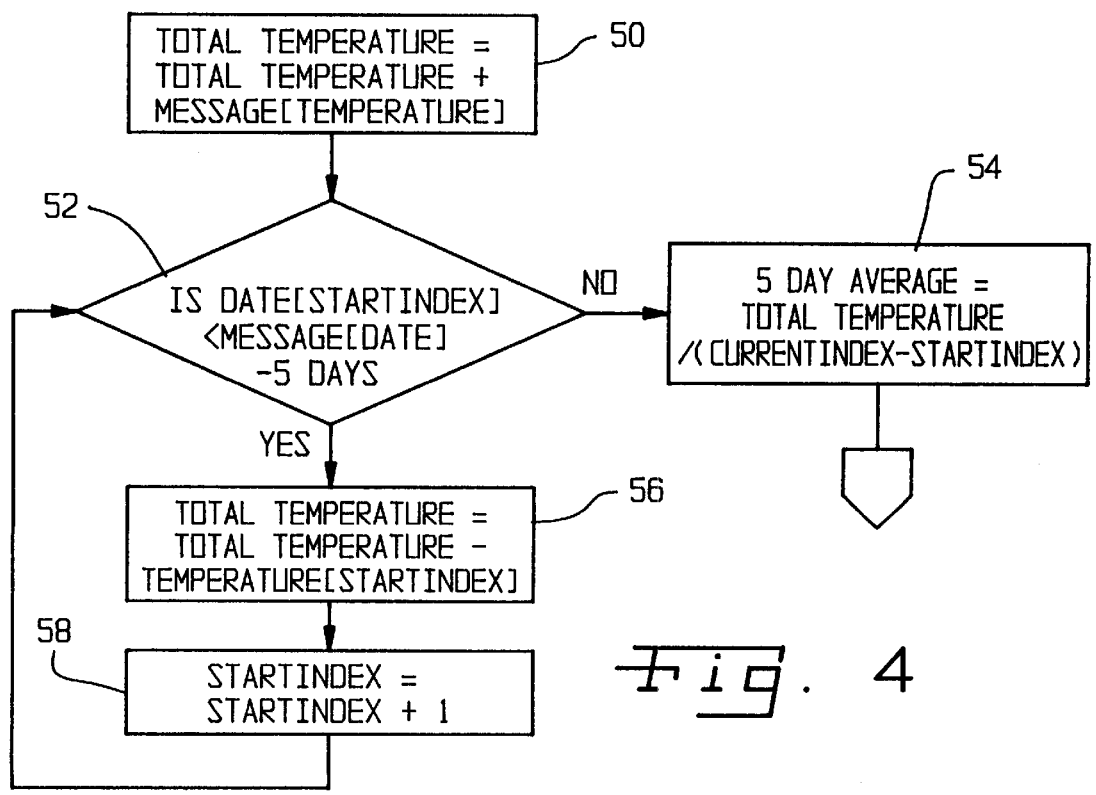
FIG. 4 is a flowchart illustrating an embodiment of the method of the present invention for determining a five day average of the core body temperature of the ruminant animal.

At block 18 a five day average is calculated. Referring more particularly to FIG. 4 corresponding thereto, a variable total temperature is increased by the temperature value of the currently parsed message contained at the pointer value MESSAGE [TEMPERATURE] (block 50). The date data for the present message stored at the memory location MESSAGE[DATE] minus five days is compared with the date data which is stored at the memory location DATE [STARTINDEX] (decision block 52). If the result from decision block 52 is NO, meaning that the date of the presently parsed message is less than five days older than the date at which the last five day average was calculated (which may occur since the data is transmitted from the bolus somewhat randomly), then a new five day average is calculated as shown in block 54. In particular, the five day average is calculated by dividing the variable total temperature by the number of temperature data received since the last five day average was calculated, as represented by the difference CURRENTINDEX-STARTINDEX.

On the other hand, if the result from decision block 52 is YES, meaning that a time period of more than five days has elapsed since the last five day average was calculated, then the value of the temperature at the memory location corresponding to the pointer STARTINDEX is subtracted from the variable TOTAL TEMPERATURE (block 56). In other words the variable TOTAL TEMPERATURE is represented by a sliding window of temperature data for tne last five days, and any temperature data older than five days is subtracted from the variable TOTAL TEMPERATURE. At block 58 the pointer integer value STARTINDEX is incremented by one.

At block 20 the variable DELTA is calculated by subtracting the five day average temperature from the one day average temperature. It is necessary to compute the difference in this manner, (i.e., one day average minus five day average) so that it can be determined whether the one day average temperature of the cow is increasing or decreasing. A change in the physiological state of the cow corresponding to standing heat or sickness will cause the one day average to increase, while a change in the physiological state corresponding to calving will cause the one day average to decrease. Similarly, a change in the physiological state associated with heat stress will cause the core body temperature of the cow to increase.

At decision blocks 22, 26 and 30, the variable DELTA and the temperature for the presently parsed message are compared with threshold values to determine whether the physiological state of the cow meets certain criteria. More particularly, at decision block 22, the variable DELTA is compared with a value THRESHOLD 1. The value THRESHOLD 1 corresponds to a physiological state in which the cow is in standing heat and is ready to be bred at that time or within a few hours by a bull or by artificial insemination. By knowing that the cow is in heat, the cow may be separated from the herd and placed in a separate breeding pen with the bull or artificially inseminated. It has been found through empirical testing that the value of THRESHOLD 1 may vary dependent upon certain factors such as the breed of cow, season of the year, etc. For example, the value of THRESHOLD 1 may vary between 0.25° F. and 1.5° F. dependent upon the breed of the cow. Thus, although the value of THRESHOLD 1 is generally constant for a specific cow, the value of THRESHOLD 1 may vary from one cow to another. Testing to date has indicated that a value of THRESHOLD 1 for an angus cow may be approximately 0.25° F. while the value of THRESHOLD 1 for a holstein cow may be approximately 0.5° F. If the result from decision block 22 is YES, then a visual indicator on a display screen for that cow is provided in the form of a yellow box or cell (block 24, as will be described in more detail hereinafter).

In the embodiment shown in FIG. 2, the constant THRESHOLD 1 corresponds to a standing heat threshold value. However, the constant Threshold 1 may also correspond to a sickness threshold value indicating that the core body temperature of the cow has increased to a point indicating sickness. A sickness threshold value is generally set at a level that is higher than the standing heat threshold value. For example, a sickness threshold value may be set at approximately 2° F. above the normal core body temperature of the cow. Alternatively, an additional decision block may be added to the method shown in FIG. 2 (such as between decision blocks 22 and 26) so that the calculated value of DELTA is compared with both a threshold value corresponding to standing heat and a threshold value corresponding to sickness.

At decision block 26, the variable DELTA is compared with a constant THRESHOLD 2. It has been found that a few hours prior to calving, a core body temperature of a cow will drop from the normal core body temperature. The constant THRESHOLD 2 thus corresponds to an empirically determined value indicating that the cow is about to calve, thereby allowing the individual to intervene and place the cow within a calving pen, or at least check on the cow to ensure that no problems are encountered. For example, if the variable DELTA is between -1° F. and -2° F., then the cow may be ready to calve. If the result from decision blocks 26 is YES, then a visual display in the form of an orange block or cell on a display monitor for that individual cow is provided to the user (block 28).

Although the constant THRESHOLD 2 is described as corresponding to a calving threshold value, it will also be appreciated that using a known gestation period, an individual may quickly determine whether the cow is in fact due to calve. If the cow is not due to calve, and the result from decision block 26 is nonetheless YES, then the result from decision block 26 may indicate another physiological state, such as hypothermia or a dead cow. Of course, it will be appreciated that additional decision blocks may be inserted into the method shown in FIG. 2 for these particular physiological states.

At decision block 30, the actual value of the parsed message (not the DELTA between the one day average and five day average) is compared with a constant THRESHOLD 3. The constant THRESHOLD 3 corresponds to a physiological state in which the cow has been exposed to high temperatures and is experiencing heat stress, such as may occur on a hot day if the cow is not provided proper shelter, ventilation and/or water. Of course, the specific value of the constant THRESHOLD 3 may vary from one breed to another, from one geographic region to another, from one season of the year to another. Heat stress is particularly important in the dairy industry, since heat stress may cause the milk production of a dairy cow to decrease for several days. If the result from decision block 30 is YES, then a visual indication in the form of a red block or cell on a display screen is provided to the user (block 32). The user may then intervene to attempt to correct the situation by sprinkling the animals with water, ventilating the animals, etc. Alternatively, in another embodiment (not shown), an additional control block may be provided on the output side of decision block 30 if the result is YES, which allows the remote receiver unit to automatically attempt to remedy the situation, such as by automatically actuating exhaust fans or a sprinkler system within a building.

If the result of each of decision blocks 22, 26 and 30 is NO, then the computed variable DELTA has not exceeded either of the constants THRESHOLD 1 or THRESHOLD 2 and the specific temperature of the parsed message has not exceeded the constant THRESHOLD 3. Thus, the physiological state of the cow is determined to be normal and a visual indication in the form of a green block or cell is provided on a display monitor to the user for that specific cow (block 34).

At block 36, an individual data point corresponding to the temperature of the parsed message is plotted on a display screen, as will be described in more detail hereinafter. The data point may correspond to the actual value of the sensed temperature, the value of the calculated DELTA, the one day average or the five day average. In the embodiment shown, the data point corresponds to the calculated one day average.

Referring now to FIG. 5, there is shown a portion of a display screen which may displayed to a user. The hatching within the boxes corresponds to the standard hatching for different colors. Thus, it may be seen that the majority of the boxes correspond to green, meaning that the physiological state of the cow is normal and unchanged, while a single box for each of the three different cows corresponds to yellow, orange and red, meaning that a corresponding threshold value has been exceeded. By providing a visual display in the manner as shown in FIG. 5, it is not necessary for the user to interpret data to determine the physiological state of the cow. The user may simply look at the screen for a particular cow and a particular day to determine if the physiological state is normal, or has changed to a condition requiring intervention or attention. However, it may also be observed that for each of the cells shown in FIG. 5, data points are also present within each cell. By clicking on a specific cell with a mouse, the user is allowed to display the data points for that cell on an entire display screen, thereby allowing the user to actually view and interpret the data if necessary or desired. Thus, although the method of displaying the physiological state of the cow is very simple and does not require data analysis or interpretation, it is also possible for a more sophisticated user to actually analyze and interpret the data as appropriate. For example, the data for a specific cell may be displayed in a manner similar to that shown in FIG. 1.

During use, the bolus which has previously been placed within the stomach of a cow transmits a message on a somewhat random basis to a remote receiver unit such as a stationary base unit. The message is parsed to ascertain the cow identification number, time stamp data, and temperature data. A one day average temperature and five day average temperature are calculated using the procedure set forth in FIGS. 3 and 4 described above. A DELTA value representing the difference between the one day average and five day average as well as the value of the sensed temperature, are compared with respective threshold values associated therewith. If a particular threshold value is exceeded, then an updated visual display indicating a physiological change in the state of the animal is displayed within a cell of a display monitor by changing the color of the monitor. If the user requires additional detailed information concerning the physiological state of the animal, a cell on the display screen may be clicked on with a mouse to expand the data associated therewith to a full screen display with all sensed data points for the relevant time period. The user may intervene or check on the state of the animal if necessary. Alternatively, in an embodiment not shown, the remote receiver unit may automatically control the environmental conditions of the animal housing to reduce the effects of a sensed physiological state such as heat stress.

In the embodiment of the method of determining a physiological state of a cow as described above, the transmit times from the ingested bolus to the remote receiver unit are somewhat random based upon a seed value which is set by a user. The seed value, in the embodiment shown, may be adjusted between two seconds to nine hours. Of course, it will be appreciated that the longer the seed value time, the less data will be received with an associated reduction in accuracy. Contrarily, the smaller the seed value time, the accuracy of the data is improved, but computing time and memory storage requirements are also increased. A seed value time of between 2 minutes and 30 minutes has been found to be particularly acceptable, with a seed value of approximately 7.5 minutes currently being used.

Moreover, in the embodiment shown, the user is provided with an indication of the physiological state of the animal using a display screen with a simplified layout and design which does not require data interpretation. However, it will also be appreciated that if a specific threshold value is exceeded, an additional type of indicator may be provided to the user to indicate that a particular physiological state has been sensed. For example, an indicator in the form of an audible alarm or digitally recorded message may easily be provided to the user if a threshold value is exceeded.

Additionally, in the embodiment shown, each bolus is placed within the stomach of a corresponding cow to send temperature data to the remote receiver unit. In another embodiment, a bolus containing a transmitter and a temperature sensor may simply be placed on a shelf or other suitable location where a herd of cattle are located. The bolus thus senses ambient temperature conditions and transmits a signal corresponding thereto to the remote receiver unit. The identification number in the message which is parsed by the receiver unit can easily be assigned such that the procedure recognizes that the bolus responds to ambient temperatures and not temperatures within the stomach of a cow. The ambient temperatures, or an ambient temperature swing during a relatively short time period, may have an effect on the one or more threshold values used in the method of the present invention. Thus, it may be possible to modify one or more of the threshold values dependent upon the sensed ambient temperature.

Further, in the embodiment shown, the one day average temperature and the five day average temperature are calculated using all data points within corresponding time periods associated therewith. In another embodiment represented in phantom lines in FIG. 2, extreme high and low data values associated with bad data or with data outside a given range may be filtered out using known data clipping techniques (block 60). For example, temperature data associated with a cow drinking extremely cold water which causes the temperature to plummet below a certain level below the normal core body temperature may be filtered out.

Furthermore, in the embodiment shown, the one day average temperature and the five day average temperature are mathematically analyzed relative to each other using a simple average temperature calculation over respective given time periods. It should also be appreciated that other mathematical analysis techniques may be used to analyze the sensed temperature data and determine a particular physiological state of the animal or a change in the physiological state of the animal. For example, it may be observed that the slope of the line graph of the temperature data in FIG. 1 sharply falls when the cow takes a drink of water, while the slope of the line between adjacent points when the stomach temperature is closer to the core body temperature is much less. It may be possible using statistical process techniques or numerical analysis techniques to analyze the data based upon the slope of the line at any point in time to determine the physiological state of the animal. Alternatively, it may be possible to use different data curve fitting techniques to eliminate data or better approximate data without decreasing the sensitivity of detecting a physiological state of the animal. An important criteria is that the data is mathematically analyzed using the past history of data for a cow.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of determining a physiological state of a ruminant animal by monitoring the core body temperature of the ruminant animal, comprising the steps of:
   providing a bolus within a stomach of the ruminant animal, said bolus including a temperature sensor and a transmitter;
   sensing a plurality of temperatures within the stomach using said sensor, each said temperature representing a temperature at a respective discrete point in time over a time period at least two of said discrete points in time being different points in time relative to each other;
   transmitting a plurality of air-borne signals to a remote receiver using said transmitter, each said air-borne signal representing at least one of said sensed temperatures;
   mathematically analyzing a plurality of said temperatures at said discrete points in time over said time period using said remote receiver; and
   determining the physiological state of the ruminant animal using said mathematically analyzed temperatures.

2. A method of determining a physiological state of a ruminant animal by monitoring the core body temperature of the ruminant animal, comprising the steps of:
   providing a bolus within a stomach of the ruminant animal, said bolus including a temperature sensor and a transmitter;
   sensing a plurality of temperatures within the stomach using said sensor, each said temperature representing a temperature at a respective discrete point in time over a time period;
   transmitting a plurality of air-borne signals to a remote receiver using said transmitter, each said air-borne signal representing at least one of said sensed temperatures;
   mathematically analyzing a plurality of said temperatures at said discrete points in time over said time period using said remote receiver, said mathematically analyzing step comprising the substep of determining an average core body temperature over said time period; and
   determining the physiological state of the ruminant animal using said mathematically analyzed temperatures.

3. The method of claim 2, wherein said average core body temperature is determined by adding values of said sensed temperatures together over said time period and dividing a total of said added values by a number of said sensed temperatures over said time period.

4. The method of claim 2, wherein said mathematically analyzing step comprises the substep of determining an average core body temperature over an extended time period.

5. The method of claim 4, wherein said mathematically analyzing step comprises the substeps of:
   determining said average core body temperature over said time period by adding values of said sensed temperatures together over said time period and dividing a total of said added values by a number of said sensed temperatures over said time period;
   determining said average core body temperature over said extended time period by adding values of said sensed temperatures together over said extended time period and dividing a total of said added values by a number of said sensed temperatures over said extended time period; and
   mathematically analyzing said average core body temperature over said time period with said average core body temperature over said extended time period.

6. The method of claim 5, wherein said mathematically analyzing step comprises the substep of calculating a difference representing said average core body temperature over said time period minus said average core body temperature over said extended time period.

7. The method of claim 6, wherein said mathematically analyzing step comprises the further substep of comparing said difference with at least one threshold value.

8. The method of claim 7, wherein said at least one threshold value comprises a plurality of threshold values representing different physiological states of the ruminant animal.

9. The method of claim 8, wherein said plurality of threshold values include a standing heat threshold value, a sickness threshold value, a heat stress threshold value, and a calving threshold value.

10. The method of claim 4, wherein each of said time period and said extended time period extend back in time from a last temperature sensed using said sensor.

11. The method of claim 10, wherein said time period is 1 day and said extended time period is 5 days.

12. A method of determining a physiological state of a ruminant animal by monitoring the core body temperature of the ruminant animal, comprising the steps of:
   providing a bolus within a stomach of the ruminant animal, said bolus including a temperature sensor and a transmitter;
   sensing a plurality of temperatures within the stomach using said sensor, each said temperature representing a temperature at a respective discrete point in time over a time period;
   transmitting a plurality of air-borne signals to a remote receiver using said transmitter, each said air-borne signal representing at least one of said sensed temperatures;
   mathematically analyzing a plurality of said temperatures at said discrete points in time over said time period using said remote receiver; and
   determining the physiological state of the ruminant animal using said mathematically analyzed temperatures;
   wherein said mathematically analyzing step and said determining step are repeated to determine a plurality of physiological states of the ruminant animal at different points in time, and wherein said remote receiver includes a visual display, and comprising the further step of providing a non-numeric visual indication of at least one of said plurality of physiological states with said visual display.

13. The method of claim 12, wherein each said sensed temperature represents a temperature at a respective discrete point in time in one of a plurality of time periods, and wherein said visual display is graphically divided into a plurality of cells, each said cell corresponding to a different said time period, each said cell being selectively displayed in one of a plurality of different colors, each said color corresponding to a respective said physiological state.

14. The method of claim 13, wherein at least one of said cells is selectively displayed in a flashing color.

15. The method of claim 12, comprising the further step of actuating an audible alarm representing one of said plurality of physiological states.

16. A method of determining a physiological state of a ruminant animal by monitoring the core body temperature of the ruminant animal, comprising the steps of:
 providing a bolus within a stomach of the ruminant animal, said bolus including a temperature sensor and a transmitter;
 sensing a plurality of temperatures within the stomach using said sensor, each said temperature representing a temperature at a respective discrete point in time over a time period, each of said discrete points in time being different points in time relative to each other;
 transmitting a plurality of air-borne signals to a remote receiver using said transmitter, each said air-borne signal representing at least one of said sensed temperatures;
 mathematically analyzing a plurality of said temperatures at said discrete points in time over said time period using said remote receiver; and
 determining the physiological state of the ruminant animal using said mathematically analyzed temperatures.

17. A method of determining a physiological state of a ruminant animal by monitoring the core body temperature of the ruminant animal, comprising the steps of:
 providing a bolus within a stomach of the ruminant animal, said bolus including a temperature sensor and a transmitter;
 sensing a plurality of temperatures within the stomach using said sensor, each said temperature representing a temperature at a respective discrete point in time over a time period;
 transmitting a plurality of air-borne signals to a remote receiver using said transmitter, each said air-borne signal representing at least one of said sensed temperatures, each of said air-borne signals corresponding to one of said sensed temperatures;
 mathematically analyzing a plurality of said temperatures at said discrete points in time over said time period using said remote receiver; and
 determining the physiological state of the ruminant animal using said mathematically analyzed temperatures.

18. A method of determining a physiological state of a ruminant animal by monitoring the core body temperature of the ruminant animal, comprising the steps of:
 providing a bolus within a stomach of the ruminant animal, said bolus including a temperature sensor and a transmitter;
 sensing a plurality of temperatures within the stomach using said sensor, each said temperature representing a temperature at a respective discrete point in time over a time period;
 transmitting a plurality of air-borne signals to a remote receiver using said transmitter, each said air-borne signal representing at least one of said sensed temperatures, each of said air-borne signals comprising a data packet;
 mathematically analyzing a plurality of said temperatures at said discrete points in time over said time period using said remote receiver; and
 determining the physiological state of the ruminant animal using said mathematically analyzed temperatures.

19. The method of claim 18, wherein each of said data packets include data representing an identification of the ruminant animal associated therewith.

20. The method of claim 19, wherein each of said data packets include data representing said discrete point in time at which said corresponding temperature is sensed.

21. A method of determining a physiological state of a ruminant animal by monitoring the core body temperature of the ruminant animal, comprising the steps of:
 providing a bolus within a stomach of the ruminant animal, said bolus including a temperature sensor and a transmitter;
 sensing a plurality of temperatures within the stomach using said sensor, each said temperature representing a temperature at a respective discrete point in time over a time period;
 transmitting a plurality of air-borne signals to a stationary base unit using said transmitter, each said air-borne signal representing at least one of said sensed temperatures;
 mathematically analyzing a plurality of said temperatures at said discrete points in time over said time period using said stationary base unit; and
 determining the physiological state of the ruminant animal using said mathematically analyzed temperatures.

22. A method of determining a physiological state of a ruminant animal by monitoring the core body temperature of the ruminant animal, comprising the steps of:
 providing a bolus within a stomach of the ruminant animal, said bolus including a temperature sensor and a transmitter;
 sensing a plurality of temperatures within the stomach using said sensor, each said temperature representing a temperature at a respective discrete point in time over a time period;
 transmitting a plurality of air-borne signals to a portable hand-held unit using said transmitter, each said air-borne signal representing at least one of said sensed temperatures;
 mathematically analyzing a plurality of said temperatures at said discrete points in time over said time period using said portable hand-held unit; and
 determining the physiological state of the ruminant animal using said mathematically analyzed temperatures.

23. A method of determining a physiological state of a ruminant animal by monitoring the core body temperature of the ruminant animal, comprising the steps of:
 providing a bolus within a stomach of the ruminant animal, said bolus including a temperature sensor and a transmitter;
 sensing a plurality of temperatures within the stomach using said sensor, each said temperature representing a temperature at a respective discrete point in time;
 transmitting a plurality of air-borne signals to a remote receiver using said transmitter, each said air-borne signal representing at least one of said sensed temperatures;
 determining an average core body temperature over a time period using said remote receiver by adding values of said sensed temperatures together over said time period and dividing a total of said added values by a number of said sensed temperatures over said time period;

determining an average core body temperature over an extended time period using said remote receiver by adding values of said sensed temperatures together over said extended time period and dividing a total of said added values by a number of said sensed temperatures over said extended time period;

mathematically analyzing said average core body temperature over said time period with said average core body temperature over said extended time period; and determining the physiological state of the ruminant animal using said mathematical analysis.

24. The method of claim 23, wherein said mathematically analyzing step comprises the substep of calculating a difference representing said average core body temperature over said time period minus said average core body temperature over said extended time period.

25. The method of claim 24, wherein said mathematically analyzing step comprises the further substep of comparing said difference with at least one threshold value.

* * * * *

UNITED STATES PATENT AND TRADEMARK OFFICE
CERTIFICATE OF CORRECTION

PATENT NO. : 6,059,733
DATED : May 9, 2000
INVENTOR(S) : Scott A. Brune, et al.

It is certified that error appears in the above-identified patent and that said Letters Patent is hereby corrected as shown below:

Column 5

Line 20, delete "tne" and substitute --the-- therefor.

Column 9

Line 25, delete "periodat" and substitute -- period, at-- therefor.

Signed and Sealed this

Third Day of April, 2001

Attest:

NICHOLAS P. GODICI

Attesting Officer

Acting Director of the United States Patent and Trademark Office